United States Patent
Stone

(10) Patent No.: US 7,595,377 B2
(45) Date of Patent: *Sep. 29, 2009

(54) SUBSTANTIALLY NON-IMMUNOGENIC INJECTABLE COLLAGEN

(75) Inventor: Kevin R. Stone, Mill Valley, CA (US)

(73) Assignee: Crosscart, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/413,360

(22) Filed: Apr. 28, 2006

(65) Prior Publication Data

US 2006/0194733 A1    Aug. 31, 2006

Related U.S. Application Data

(63) Continuation of application No. 10/722,869, filed on Nov. 26, 2003, now Pat. No. 7,064,187.

(60) Provisional application No. 60/429,078, filed on Nov. 26, 2002.

(51) Int. Cl.
  *C07K 1/14* (2006.01)
  *A61K 38/17* (2006.01)

(52) U.S. Cl. ...................... 530/355; 530/356

(58) Field of Classification Search .................. 530/356, 530/350

See application file for complete search history.

(56) References Cited

U.S. PATENT DOCUMENTS 3,949,073 A * 4/1976 Daniels et al. .................. 514/2
5,171,574 A * 12/1992 Kuberasampath et al. ... 424/423
5,989,498 A * 11/1999 Odland ........................ 422/22

OTHER PUBLICATIONS

Associates in Otolaryngology. The Science of Collagen (2005). www.entdr.com/collagen.html.*
Spira et al. Human amnion collagen for soft tissue augementation—biochemical characterizations and animal observations. Journal of Biomedical Materials Research. 1994. vol. 28, No. 1, pp. 91-96.*
Zyderm Collagen Implant Physician Package Insert—2006 http://www.allerganandinamed.com/pdf/us_aesthetics/M761A_Zyderm_DFU.pdf#search=%22Zyderm%201%22.*
Matton et al, The History of Injectable Biomaterials and the Biology of Collagen. Aesthetic Plastic Surgery. 1985. vol. 9, pp. 133-140.*
Meriam-Webster On-line Dictionary Definition of "Substantial". www.m-w.com/dictionary/substantially. No date.*

* cited by examiner

*Primary Examiner*—Suzanne M. Noakes
(74) *Attorney, Agent, or Firm*—John M. Garvey; Matthew L. Fenselau; Foley & Lardner LLP

(57) ABSTRACT

The invention provides an article of manufacture comprising a substantially non-immunogenic injectable collagen for implantation into humans. The invention further provides methods for preparing injectable collagen material by removing collagen-containing material from a non-human animal; washing in saline and alcohol; subjecting material to cellular disruption treatment; and digesting the material with a proteoglycan-depleting factor and/or glycosidase and optionally following with a capping treatment. The invention also provides an article of manufacture produced by the method. The injectable collagen material of the invention are substantially non-immunogenic and have substantially the same mechanical properties as a corresponding native soft tissue.

6 Claims, No Drawings

SUBSTANTIALLY NON-IMMUNOGENIC INJECTABLE COLLAGEN

CROSS REFERENCE TO RELATED APPLICATIONS

This application is a continuation application from U.S. Pat. No. 7,064,187 filed Nov. 26, 2003, which claims priority to and the benefit of U.S. provisional application No. 60/429,078, filed on Nov. 26, 2002, which are all hereby incorporated herein by reference.

FIELD OF THE INVENTION

The present invention relates to the field of treatment of defective human tissue, and in particular, to replacement and repair of defective or damaged human tissue using a substantially non-immunogenic injectable collagen from a non-human animal.

BACKGROUND OF THE INVENTION

Injectable collagen is a material that is made from the connective tissue of cows or pigs that is injected into and under the skin for cosmetic purposes. Injectable collagen has been approved by the Food & Drug Administration (FDA) for filling in "contour deformities" in the skin such as acne scars and wrinkles. Injectable collagen might also be used for "augmentation", that is, for enlarging otherwise normal facial features, and to correct wrinkles on the skin bordering the lips.

However, some people are allergic to collagen and collagen-containing products, such as surgical sutures and sponges. Collagen allergies can take the form of rash, hives, joint and muscle pain, headache, and, in a few cases, severe reactions that include shock and difficulty breathing. Other adverse effects that have occurred after collagen injections, and which appear to have been related to the injections, include infections, abscesses, open sores, lumps, peeling of the skin, scarring, recurrence of herpes simplex, and partial blindness. Some people with connective tissue diseases can have an increased risk of severe allergic reactions to collagen injections. These connective tissue diseases include rheumatoid arthritis, scleroderma, juvenile rheumatoid arthritis, and polymyositis and dermatomyositis, which are chronic, progressive inflammatory disorders. Other people may be allergic to collagen and not know it. The collagen allergy test is not perfect; some people who do not react to the test develop allergies during the course of collagen treatment.

Accordingly, there is a need in the art for an injectable collagen material with reduced immunogenicity.

SUMMARY OF THE INVENTION

The invention provides a substantially non-immunogenic collagen-containing material for injection into a human, for example, for soft tissue augmentation. The invention further provides methods for processing xenogeneic collagen material with reduced immunogenicity. The methods of the invention, include, alone or in combination, treatment with radiation, one or more cycles of freezing and thawing, treatment with a chemical cross-linking agent, treatment with alcohol. In addition to or in lieu of these methods, the methods of the invention include, alone or in combination, in any order, a cellular disruption treatment, glycosidase digestion of carbohydrate moieties of the collagen-containing material, or treatment with proteoglycan-depleting factors. Optionally, the glycosidase digestion or proteoglycan-depleting factor treatment can be followed by further treatments, such as, for example, treatment of carbohydrate moieties of the collagen material with capping molecules. After one or more of the above described processing steps, the methods of the invention provide a collagen-containing material.

In one embodiment, the invention provides an article of manufacture comprising a substantially non-immunogenic injectable collagen-containing material for implantation into a human.

In another embodiment, the invention provides a method of preparing a collagen-containing material for injection into a human, which includes removing at least a portion of a collagen-containing material from a non-human animal; washing the collagen-containing material in water and alcohol; subjecting the collagen-containing material to a cellular disruption treatment; and digesting the collagen-containing material with a glycosidase to remove first surface carbohydrate moieties.

In another embodiment, the invention provides a method of preparing a collagen-containing material for injection into a human, which includes removing at least a portion of a collagen-containing material from a non-human animal; washing the collagen-containing material in water and alcohol; and subjecting the collagen-containing material to at least one treatment selected from the group consisting of exposure to ultraviolet radiation, immersion in alcohol and/or freeze/thaw cycling.

In a further embodiment, the invention provides a method of preparing collagen-containing material for injection into a human, which includes removing at least a portion of collagen-containing material from a non-human animal; washing the collagen-containing material in water and alcohol; subjecting the collagen-containing material to a cellular disruption treatment; and digesting the collagen-containing material with a proteoglycan-depleting factor to remove at least a portion of the proteoglycans from the collagen-containing material.

In another embodiment, the invention provides collagen-containing material for implantation into a human which includes a collagen-containing material from a non-human animal, wherein the portion has substantially no surface carbohydrate moieties which are susceptible to glycosidase digestion. In yet another embodiment, the invention provides a collagen-containing material for implantation into a human which includes a collagen-containing material from a non-human animal, wherein the portion includes extracellular components and substantially only dead cells, the extracellular components and dead cells having substantially no surface α-galactosyl moieties and having capping molecules linked to at least a portion of surface carbohydrate moieties. The portion of the soft tissue is substantially non-immunogenic.

In still yet another embodiment, the invention provides a collagen-containing material for implantation into a human which includes collagen-containing material from a non-human animal, wherein the portion includes extracellular components and substantially only dead cells, the extracellular components having reduced proteoglycans. The collagen-containing material is substantially non-immunogenic.

These compositions and methods are useful in treating human requiring soft tissue augmentation. Accordingly, these methods find use in human and other mammalian subjects requiring such treatment. Soft tissue augmentation includes subcutaneous delivery, intradermal delivery and subdermal delivery of the compositions. In addition, delivery of the compositions to sphincter sites in vivo is contemplated including delivery to the esophageal sphincter, the anal sphincter, and the like.

DETAILED DESCRIPTION OF THE PREFERRED EMBODIMENTS

Definitions

"Xenotransplantation" is a procedure that involves the transplantation, implantation, injection or infusion into a human recipient of either (a) live cells, tissues, or organs from a nonhuman animal source or (b) human body fluids, cells, tissues or organs that have had ex vivo contact with live nonhuman animal cells, tissues, or organs. Tissue for allograft transplantation is commonly cryopreserved to optimize cell viability during storage, as disclosed, for example, in U.S. Pat. Nos. 5,071,741; 5,131,850; 5,160,313 and No. 5,171,660, each incorporated by reference. Xenotransplantation includes the injection of xenogeneic collagen-containing material into a human.

As used herein, the term "xenograft" is synonymous with the term "heterograft" and refers to a graft transferred from an animal of one species to one of another species. *Stedman's Medical Dictionary* (Williams & Wilkins, Baltimore, Md., 1995). As used herein, the term "xenogeneic", refers to tissue transferred from an animal of one species to one of another species. Id. Transplants made from one person or animal to another in the same species ("allogeneic"); Sengupta et al., *J. Bone Suro.* 56B(1):167-177 (1974); Rodrigo et al., *Clin Orth.* 134:342-349 (1978).

Once implanted in an individual, a xenograft can provoke immunogenic reactions, such as chronic or hyperacute rejection. The term "chronic rejection", as used herein refers to an immunological reaction in an individual against a xenograft being implanted into the individual. Typically, chronic rejection is mediated by the interaction of IgG natural antibodies in the serum of the individual receiving the xenograft and carbohydrate moieties expressed on cells, and/or cellular matrices and/or extracellular components of the xenograft. For example, transplantation of soft tissue cartilage xenografts from nonprimate mammals (e.g., porcine or bovine origin) into humans is primarily prevented by the interaction between the IgG natural anti-Gal antibody present in the serum of humans with the carbohydrate structure Gal$\alpha$1-3Gal$\beta$1-4GlcNAc-R ($\alpha$-galactosyl or $\alpha$-gal epitope) expressed in the xenograft. K. R. Stone et al., *Transplantation* 63: 640-645 (1997); U. Galili et al., *Transplantation* 63: 646-651 (1997). In chronic rejection, the immune system typically responds within one to two weeks of implantation of the xenograft. A "hyper acute rejection" as used herein, refers to the immunological reaction in an individual against a xenograft being implanted into the individual, where the rejection is typically mediated by the interaction of IgM natural antibodies in the serum of the individual receiving the xenograft and carbohydrate moieties expressed on cells. This interaction activates the complement system causing lysis of the vascular bed and stoppage of blood flow in the receiving individual within minutes to two to three hours.

The term "soft tissue augmentation" includes, but is not limited to, the following: dermal tissue augmentation; filling of lines, folds, wrinkles, minor facial depressions, cleft lips and the like, especially in the face and neck; correction of minor deformities due to aging or disease, including in the hands and feet, fingers and toes; augmentation of the vocal cords or glottis to rehabilitate speech; dermal filling of sleep lines and expression lines; replacement of dermal and subcutaneous tissue lost due to aging; lip augmentation; filling of crow's feet and the orbital groove around the eye; breast augmentation; chin augmentation; augmentation of the cheek and/or nose; filling of indentations in the soft tissue, dermal or subcutaneous, due to, e.g., overzealous liposuction or other trauma; filling of acne or traumatic scars and rhytids; filling of nasolabial lines, nasoglabellar lines and infraorallines.

The term "biocompatible polymer" refers to polymers which have a water equilibrium content of less than about 15% and which, in the amounts employed, are non-toxic, non-peptidyl, chemically inert, and substantially non-immunogenic when used internally in the mammal and which are substantially insoluble in the tissue. The biocompatible polymers do not substantially decrease in volume over time and, since the polymer forms a solid inert mass, it does not migrate to distant organs within the body. Suitable biocompatible polymers include, by way of example, cellulose acetates [including cellulose diacetate, ethylene vinyl alcohol copolymers], polyalkyl acrylates, acrylate copolymers, polyalkyl alkacrylates, and the like.

The term "biocompatible solvent" refers to an organic material liquid at least at body temperature of the mammal in which the biocompatible polymer is soluble and, in the amounts used, is substantially non-toxic. Suitable biocompatible solvents include, by way of example, ethyl lactate, analogues/homologues/isomers of ethyl lactate, dimethylsulfoxide, analogues/homologues of dimethylsulfoxide, ethanol, acetone, and the like. Aqueous mixtures with the biocompatible solvent can also be employed provided that the amount of water employed is sufficiently small that the dissolved polymer precipitates upon contact with tissue fluids. The biocompatible solvent can be ethyl lactate or dimethylsulfoxide.

As used herein, the term "capping molecule(s)", refers to molecule(s) which link with carbohydrate chains such that the collagen-containing material is no longer recognized as foreign by the subject's immune system.

As used herein, the terms "to cap" or "capping", refer to linking a capping molecule such as a carbohydrate unit to the end of a carbohydrate chain, as in, for example, covalently linking a carbohydrate unit to surface carbohydrate moieties on the collagen-containing material.

As used herein, the term "portion", as in, for example, a portion of soft tissue, second surface carbohydrate moieties or proteoglycans, refers to all or less than all of the respective soft tissue, second surface carbohydrate moieties or proteoglycans of the collagen-containing material.

As used herein, the term "first surface carbohydrate moiety (moieties)" refers to a terminal $\alpha$-galactosyl sugar at the non-reducing end of a carbohydrate chain.

As used herein, the term "second surface carbohydrate moiety (moieties)" refers to a N-acetyllactosamine residue at the non-reducing end of a carbohydrate chain, the residue being noncapped either naturally or as a result of prior cleavage of an $\alpha$-galactosyl epitope.

As used herein, the term "cellular disruption" as in, for example, cellular disruption treatment, refers to a treatment for killing cells. Collagen-containing material obtained from xenograft tissues may also be subjected to various physical treatments in preparation for implantation. Tissue for allograft transplantation is commonly cryopreserved to optimize cell viability during storage, as disclosed, for example, in U.S. Pat. Nos. 5,071,741; 5,131,850; 5,160,313; and U.S. Pat. Nos. 5,171,660. 5,071,741 discloses that freezing tissues causes mechanical injuries to cells therein because of extracellular or intracellular ice crystal formation and osmotic dehydration. The term "extracellular components", as used herein, refers to any extracellular water, collagen and elastic fibers, proteoglycans, fibronectin, elastin, and other glycoproteins, such as are present in vertebrate tissue.

The term "soft tissue", as used herein, refers to cartilaginous structures, such as meniscus and articular cartilage; ligaments, such as anterior cruciate ligaments; tendons; and heart valves. Moreover, the femoral condyles articulate with the surface plateaus of the tibia, through the cartilaginous medial and lateral menisci soft tissue, and all of these structures are held in place by various ligaments. The medial and lateral menisci are structures comprised of cells called fibrochondrocytes and an extracellular matrix of collagen and elastic fibers as well as a variety of proteoglycans.

As used herein, the term "surface carbohydrate moiety (moieties)" or "first surface carbohydrate moiety (moieties)" refers to a terminal α-galactosyl sugar at the non-reducing end of a carbohydrate chain. As used herein, the term "second surface carbohydrate moiety (moieties)" refers to a N-acetyl-lactosamine residue at the non-reducing end of a carbohydrate chain, the residue being non-capped either naturally or as a result of prior cleavage of an α-galactosyl epitope.

Preparation of Substantially Non-Immunogenic Collagen-Containing Material

The present invention is directed against the chronic rejection of collagen-containing material for injection or implantation into humans. Accordingly, the collagen-containing material produced in accordance with the method of the invention is substantially non-immunogenic, while generally maintaining the mechanical properties of a native soft tissue.

The invention provides, in one embodiment, a method for preparing or processing a collagen-containing material. The collagen-containing material may be harvested from any non-human animal. A collagen-containing material from transgenic non-human animals or from genetically altered non-human animals may also be used in accordance with the present invention.

In the first step of the method of the invention, a collagen-containing material is removed from a non-human animal. The collagen-containing material should be collected from freshly killed animals and preferably immediately placed in a suitable sterile isotonic or other tissue preserving solution. Harvesting of the collagen-containing material should occur as soon as possible after slaughter of the animal and preferably should be performed in the cold, i.e., in the approximate range of about 5° C. to about 20° C., to minimize enzymatic degradation.

The collagen-containing material is then washed in about ten volumes of sterile cold water to remove residual blood proteins and water-soluble materials. The collagen-containing material is then immersed in alcohol at room temperature for about five minutes, to sterilize the tissue and to remove non-collagenous materials.

After alcohol immersion, the collagen-containing material may be subjected to at least one of the following treatments: radiation treatment, treatment with alcohol, one or more cycles of freezing and thawing, and/or treatment with a chemical cross-linking agent. When more than one of these treatments is applied to the collagen-containing material, the treatments may occur in any order.

In one embodiment of the method of the invention, the collagen-containing material may be treated by exposure to ultraviolet radiation for about fifteen minutes or gamma radiation in an amount of about 0.5 to 3 MegaRad.

The invention provides a method of sterilizing a substantially non-immunogenic collagen-containing material for injection or implantation into a human. The methods of the invention include, alone or in combination, treatment with radiation, one or more cycles of freezing and thawing, treatment with a chemical cross-linking agent, treatment with alcohol and sterilization. In addition to or in lieu of these methods, the methods of the invention include, alone or in combination, in any order, a cellular disruption treatment, glycosidase digestion of carbohydrate moieties of the collagen-containing material, or treatment with proteoglycan-depleting factors. Optionally, the collagen-containing material can be exposed to an aldehyde for further cross-linking after one or more of the above-described processing steps.

In one embodiment, the method of the invention is the additive combination of chemical and terminal treatments. This embodiment advantageously provides a dose validation for product irradiation sterilization, applicable to either electron beam irradiation or gamma irradiation. In a particular embodiment, electron beam level is dictated by ANSI/AAMI/ISO 11137 sterility assurance limits (10-6) through sub-lethal dose assessment. This yields a validated dose, in our case for our process of 17.8 kGy or 1.78 mRads (interchangeable, with the former terminology used industrially). The 17.8 kGy dose is consistent with publications by those skilled in the art of investigating radiation and graft integrity. Glutaraldehyde cross-linking is used to stabilize the collagen structure, attenuate immunological recognition of the graft, and is additive in sterilization effect with respect to viral inactivation.

In another embodiment, the invention provides a method of preparing a collagen-containing material for injection or implantation into a human, which includes removing collagen-containing material from a non-human animal; washing the collagen-containing material in water and alcohol; and subjecting the collagen-containing material to at least one treatment selected from the group consisting of exposure to ultraviolet radiation, immersion in alcohol and/or freeze/thaw cycling.

In a further embodiment, the invention provides a sterilized, substantially non-immunogenic collagen-containing material for injection or implantation into a human, wherein the collagen-containing material has substantially no surface carbohydrate moieties that are susceptible to glycosidase digestion.

The Center for Disease Control has suggested steps to reduce the risk for allograft associated infections. "When possible, a method that can kill bacterial spores should be used to process tissue. Existing sterilization technologies used for tissue allografts, such as gamma irradiation, or new technologies effective against bacterial spores should be considered." *MMWR* 51(10); 207-210 (Mar. 15, 2002). Also, the FDA has released new guidelines for tissue processors regarding the processing of human tissues intended for transplantation. CBER, *Guidance for Industry: Validation of Procedures for Processing of Human Tissues Intended for Transplantation* (Mar. 8, 2002).

The sterilization process of the invention provides bioburden and viral inactivation by a combination of two processing steps from the tissue treatment process described above.

The first step is a chemical sterilization treatment with glutaraldehyde, and the second step is terminal sterilization by electron beam irradiation. The chemical sterilization step involves tissue incubation in 0.10% glutaraldehyde for 9 to 16 hours at 20° C. to 25° C. Tissue glutaraldehyde penetration was validated by hydrothermal shrink temperature assay.

The second step is a terminal sterilization based on ANSI/AAMI/ISO 11137 medical device sterility assurance limits, and uses electron beam irradiation as a controlled ionizing radiation source. Medical device sterility assurance is based on validation of a sterilization process that can repeatedly produce medical devices with a sterility assurance limit that meets the current standards (SAL=$10^{-6}$).

In one embodiment of the tissue sterilization process of the invention, the collagen-containing material of the invention is terminally sterilized using E-beam ionizing radiation. For this embodiment, the validated sterilization dose of 17.8 kGy was established using ANSI/AAMI/ISO 11137-Dose Method 1 to provide a sterility assurance level of 10-6. Further, a range of sterilization dose from 15.8 to 21.3 kGy has utility as a terminal sterilization dose.

Porcine endogenous retrovirus (PERV) has been discussed as a potential risk from xenogeneic materials. Takefman D M, Wong S. Maudru et al. *J. Virol* 75(10):4551(2001). The risk of PERV can be evaluated based on three separate assays. The first assay is a standard viral inactivation assay of non-endogenous murine leukemia virus as a model virus for PERV. In the second assay, the collagen-containing material of the invention is submitted for a co-cultivation assay for PERV, according to previously published methods. Takefman D M, Wong S. Maudru et al. *J. Viral* 75(10):4551 (2001). The third assay evaluates the collagen-containing material by the following three manufacturing steps: (1) freeze/thaw (a minimum of two freeze/thaw cycles); (2) incubation with 0.10% glutaraldehyde and (3) exposure to 17.8 kGy ionizing radiation. To verify the lack of live cells in the device, a $^{35}$S labeled methionine uptake study is performed. The cellular uptake of radiolabeled methionine is measured in a scintillation counter. Live cells incorporate this labeled amino acid as part of their normal metabolism.

In another embodiment, the v may be treated by again being placed in an alcohol solution. Any alcohol solution may be used to perform this treatment. Preferably, the collagen-containing material is placed in a 70% solution of isopropanol at room temperature.

In a further embodiment of the method of the invention, the collagen-containing material may be treated by freeze/thaw cycling. For example, the v may be frozen using any method of freezing, so long as the collagen-containing material is completely frozen, i.e., no interior warm spots remain which contain unfrozen tissue. Preferably, the collagen-containing material is dipped into liquid nitrogen for about five minutes to perform this step of the method. More preferably, the collagen-containing material is frozen slowly by placing it in a freezer. In the next step of the freeze/thaw cycling treatment, the collagen-containing material is thawed by immersion in an isotonic saline bath at room temperature (about 25° C.) for about ten minutes. No external heat or radiation source is used, in order to minimize fiber degradation.

In yet a further embodiment, the collagen-containing material may optionally be exposed to a chemical agent to tan or cross-link the proteins within the extracellular components, to further diminish or reduce the immunogenic determinants present in the collagen-containing material. Any tanning or cross-linking agent may be used for this treatment, and more than one cross-linking step may be performed or more than one cross-linking agent may be used in order to ensure complete cross-linking and thus optimally reduce the immunogenicity of the collagen-containing material. For example, aldehydes such as glutaraldehyde, formaldehyde, adipic dialdehyde, and the like, may be used to cross-link the extracellular collagen of the collagen-containing material in accordance with the method of the invention. Other suitable cross-linking agents include aliphatic and aromatic diamines, carbodiimides, diisocyanates, and the like.

When an aldehyde such as, for example, glutaraldehyde is used as the cross-linking agent, the collagen-containing material may be placed in a buffered solution containing about 0.001% to about 5.0% glutaraldehyde and preferably, about 0.01% to about 5.0% glutaraldehyde, and having a pH of about 7.4. More preferably about 0.01% to about 0.10% aldehyde, and most preferably about 0.01% to about 0.05% aldehyde is used. Any suitable buffer may be used, such as phosphate buffered saline or trishydroxymethylaminomethane, and the like, so long as it is possible to maintain control over the pH of the solution for the duration of the cross-linking reaction, which may be from one to fourteen days, and preferably from one to five days, and most preferably from three to five days.

Alternatively, the collagen-containing material can be exposed to a cross-linking agent in a vapor form, including, but not limited to, a vaporized aldehyde cross-linking agent, such as, for example, vaporized formaldehyde. The vaporized cross-linking agent can have a concentration and a pH and the v can be exposed to the vaporized cross-linking agent for a period of time suitable to permit the cross-linking reaction to occur. For example, the collagen-containing material can be exposed to vaporized cross-linking agent having a concentration of about 0.001% to about 5.0% and preferably, about 0.01% to about 5.0%, and a pH of about 7.4. More preferably, the collagen-containing material is exposed to the aldehyde in an amount ranging from about 0.01% to about 0.10%, and most preferably to an aldehyde ranging in an amount from about 0.01% to about 0.05%. The collagen-containing material is exposed to the aldehyde for a period of time which can be from one to fourteen days, and preferably from one to five days, and most preferably from three to five days. Exposure to vaporized cross-linking agent can result in reduced residual chemicals in the collagen-containing material from the cross-linking agent exposure.

The cross-linking reaction should continue until the immunogenic determinants are substantially eliminated from the xenogeneic collagen-containing material. When diamines are also used as cross-linking agents, the glutaraldehyde cross-linking should occur after the diamine cross-linking, so that any unreacted diamines are capped. After the cross-linking reactions have proceeded to completion as described above, the collagen-containing material should be rinsed to remove residual chemicals, and 0.01-0.10 M glycine, and preferably, 0.01-0.05 M glycine may be added to cap any unreacted aldehyde groups which remain.

In addition to or in lieu of the above treatments, the collagen-containing material can be subjected to a cellular disruption treatment to kill the cells in the collagen-containing material. Optionally, the cellular disruption treatment precedes or follows digestion of the collagen-containing material with glycosidases to remove first surface carbohydrate moieties from the collagen-containing material. In addition or in lieu of the glycosidase treatment, either preceding or following the glycosidase treatment, the collagen-containing material is treated with proteoglycan-depleting factors. Further, the glycosidase and/or proteoglycan-depleting factor digestion in turn is optionally followed by linkage with capping molecules such as fucosyl or nacetyl glucosamine molecules to cap surface N-acetyllactosamine ends of carbohydrate chains of the collagen-containing material.

In embodiments of this method of the invention, the collagen-containing material is subjected to a cellular disruption treatment to kill the cells of the soft tissue. Typically after surface carbohydrate moieties have been removed from living cells and the extracellular components, the living cells reexpress the surface carbohydrate moieties. Reexpression of antigenic moieties of a collagen-containing material can provoke continued immunogenic rejection of the collagen-containing material. In contrast, dead cells are unable to reexpress surface carbohydrate moieties. Removal of antigenic surface carbohydrate moieties from dead cells and the extracellular components of a collagen-containing material substantially permanently eliminates antigenic surface carbohydrate moieties as a source of immunogenic rejection of the collagen-containing material.

Accordingly, in the above-identified embodiments, the collagen-containing material of the present invention is subjected to freeze/thaw cycling as discussed above to disrupt, i.e., to kill the cells of the soft tissue. Alternatively, the collagen-containing material of the invention is treated with gamma radiation having an amount of 0.2 MegaRad up to about 3 MegaRad. Such radiation kills the soft tissue cells and sterilizes the collagen-containing material. Once killed, the soft tissue cells are no longer able to reexpress antigenic surface carbohydrate moieties such α-gal epitopes which are factors in the immunogenic rejection of the injected collagen-containing material.

Either before or after the soft tissue cells are killed, in embodiments of the invention, the collagen-containing material is subjected to in vitro digestion of the collagen-containing material with glycosidases, and specifically galactosidases, such as α-galactosidase, to enzymatically eliminate antigenic surface carbohydrate moieties. In particular, α-gal epitopes are eliminated by enzymatic treatment with α-galactosidases, as shown in the following reaction:

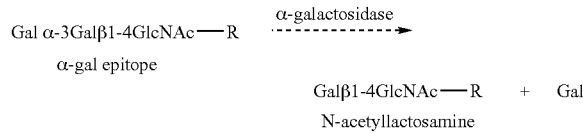

The N-acetyllactosamine residues are epitopes that are normally expressed on human and mammalian cells and thus are not immunogenic. The in vitro digestion of the collagen-containing material with glycosidases is accomplished by various methods. For example, the collagen-containing material can be soaked or incubated in a buffer solution containing glycosidase. Alternatively, a buffer solution containing the glycosidase can be forced under pressure into the collagen-containing material via a pulsatile lavage process.

Elimination of the α-gal epitopes from the collagen-containing material diminishes the immune response against the collagen-containing material. The α-gal epitope is expressed in nonprimate mammals and in New World monkeys (monkeys of South America) as $1\times10^6$-$35\times10^6$ epitopes per cell, as well as on macromolecules such as proteoglycans of the extracellular components. U. Galili et al., *J. Biol. Chem.* 263: 17755 (1988). This epitope is absent in Old World primates (monkeys of Asia and Africa and apes) and humans, however. Id. Anti-Gal is produced in humans and primates as a result of an immune response to α-gal epitope carbohydrate structures on gastrointestinal bacteria. U. Galili et al., *Infect. Immun.* 56: 1730 (1988); R. M. Hamadeh et al., *J. Clin. Invest.* 89: 1223 (1992). Since nonprimate mammals produce α-gal epitopes, xenotransplantation by injection of collagen-containing material from these mammals into primates results in rejection because of primate anti-Gal binding to these epitopes on the collagen-containing material. The binding results in the destruction of the collagen-containing material by complement fixation and by antibody dependent cell cytotoxicity. U. Galili et al., *Immunology Today* 14: 480 (1993); M. Sandrin et al., *Proc. Natl. Acad. Sci.* USA 90: 11391 (1993); H. Good et al., *Transplant. Proc.* 24: 559 (1992); B. H. Collins et al., *J. Immunol.* 154: 5500 (1995). Furthermore, xenotransplantation results in major activation of the immune system to produce increased amounts of high affinity anti-Gal. Accordingly, the substantial elimination of a-gal epitopes from cells and from extracellular components of the collagen-containing material, and the prevention of reexpression of cellular α-gal epitopes can diminish the immune response against the collagen-containing material associated with anti-Gal antibody binding with α-gal epitopes.

In addition, the collagen-containing material may be treated with polyethylene glycol (PEG) prior to or concurrently with treatment with glycosidase. PEG acts as a carrier for the glycosidase by covalently bonding to the enzyme and to the collagen extracellular components.

Either before or after the soft tissue cells are killed, in embodiments of the invention, the collagen-containing material is washed or digested with one or more different types of proteoglycan-depleting factors. The proteoglycan-depleting factor treatment can precede or follow glycosidase treatment. Proteoglycans such as glycosaminoglycans (GAGs) are interspersed either uniformly as individual molecules or within varying amounts within the extracellular components of the collagen-containing material. The GAGs include mucopolysaccharide molecules such as chondroitin 4-sulfate, chondroitin 6-sulfate, keratan sulfate, dermatan sulfate, heparin sulfate, hyaluronic acid, and mixtures thereof. The proteoglycans including such GAGs contain attached carbohydrates such as α-gal epitopes. Such epitopes stimulate an immune response once the collagen-containing material is transplanted, as discussed above. Washing or digesting the collagen-containing material with the proteoglycan-depleting factor removes at least a portion of the proteoglycans and attached a-gal epitopes from the extracellular components of the collagen-containing material, and thereby diminishes the immune response against the collagen-containing material upon its injection. After the proteoglycan-depleting factor treatment and subsequent transplantation, natural tissue can repopulate the remaining collagen shell.

Non-limiting examples of the proteoglycan-depleting factors used in the present invention include proteoglycan-depleting factors such as chondroitinase ABC, hyaluronidase, chondroitin AC II lyase, keratanase, and trypsin. Other proteoglycan-depleting factors used in the present invention include fragments of fibronectin. Homandberg et al. suggest that fibronectin fragments, such as the amino-terminal 29-kDa fragment, bind to the superficial surface of articular cartilage soft tissue and penetrate the cartilage to surround the cartilage cells. G. A. Homandberg et al., *Biochem. J.* 321: 751-757 (1997); G. A. Homandberg et al., *Osteoarthritis and Cartilage* 5: 309319 (1997); G. A. Homandberg et al., *Archives of Biochemistry and Biophysics* 311(2): 213-218 (June 1994); G. A. Homandberg et al., *Inflammation Research* 46: 467-471 (1997). At selected concentrations, Homandberg et al. further suggest that the addition of such fibronectin fragments to cartilage in vitro or in vivo results in the temporary suppression of proteoglycan synthesis and the enhancement of extracellular metalloproteinases which in turn cause a rapid proteoglycan loss from cartilage tissue. Id.

Other proteoglycan-depleting factors known to those of ordinary skill in the art are also possible for use with the present invention, however. The collagen-containing material is treated with proteoglycan-depleting factor in an amount effective for removing at least a portion of the proteoglycans from the extracellular components. Preferably, the collagen-containing material is treated with proteoglycan-depleting factor such as hyaluronidase in an amount ranging from about 1.0 TRU/ml to about 100.0 TRU/ml or proteoglycan-depleting factor such as chondroitinase ABC in an amount ranging from about 0.01 µ/ml to about 2.0 µ/ml or most preferably, in an amount ranging from about 1.0 µ/ml to about 2.0 µ/ml. The collagen-containing material can also be treated with proteoglycan-depleting factor such as fibronectin fragment, (e.g., amino terminal 29-kDa fibronectin fragment) in an amount ranging from about 0.01 µM to about 1.0 µM, and preferably in an amount ranging from about 0.1 µM to about 1.0 µM.

Following treatment with glycosidase or treatment with proteoglycan-depleting factors, the remaining carbohydrate chains (e.g., glycosaminoglycans) of the collagen-containing material are optionally treated with capping molecules to cap at least a portion of the remaining carbohydrate chains. Examples of capping molecules used in the invention include fucosyl and N-acetyl glucosamine.

Prior to injection, the collagen-containing material of the invention may be treated with limited digestion by proteolytic enzymes such as ficin or trypsin to increase tissue flexibility, or coated with anti calcification agents, antithrombotic coatings, antibiotics, growth factors, or other drugs which may enhance the incorporation of the collagen-containing material into the recipient.

Assays for α-Gal Epitopes

An ELISA assay for assessing the elimination of α-gal epitopes from collagen-containing material by α-galactosidase can be conducted.

A monoclonal anti-Gal antibody (designated M86) which is highly specific for α-gal epitopes on glycoproteins is produced by fusion of splenocytes from anti-Gal producing knockout mice for α 1,3 galactosyltransferase, and a mouse hybridoma fusion partner.

M86 binds to synthetic α-gal epitopes linked to bovine serum albumin (BSA), to bovine thyroglobulin which has 11 α-gal epitopes, R. G. Spiro et al., *J. Biol. Chem.* 259: 9858 (1984); or to mouse laminin which has 50 α-gal epitopes, R. G. Arumugham et al., *Biochem. Biophys. Acta* 883: 112 (1986); but not to human thyroglobulin or human laminin, α-Gaβ1-4 GlcNAc-BSA (N-acetyllactosamine-BSA) and Galα1-4Galβ1-4GlcNAc-BSA (P1 antigen linked to BSA), all of which completely lack α-gal epitopes. Binding is measured at different dilutions of the M86 tissue culture medium.

Once the M86 antibody is isolated, the monoclonal antibody is diluted from about 1:20 to about 1:160, and preferably diluted from about 1:50 to about 1:130. The antibody is incubated for a predetermined period of time ranging between about 5 hr to about 24 hr, at a predetermined temperature ranging from about 3° C. to about 8° C. The antibody is maintained in constant rotation with collagen-containing material. Subsequently, the collagen-containing materials are removed by centrifugation at centrifugation rate ranging from about 20,000×g to about 50,000×g. The proportion of M86 bound to the collagen-containing material is assessed by measuring the remaining M86 activity in the supernatant, in ELISA with α-gal-BSA as described in the prior art in, for example, U. Galili et al., *Transplantation* 63: 645-651 (1997). The extent of binding of M86 to the soft tissue is defined as a percentage inhibition of subsequent binding to α-gal-BSA. There is a direct relationship between the amount of α-gal epitopes in the soft tissue and the proportion of M86 complexed with the soft tissue fragments, thus removed from the supernatant (i.e., percentage inhibition).

Assay for Immune Response

The occurrence of an immune response against the collagen-containing material is assessed by determining anti-Gal and non-anti-Gal anti-soft tissue antibodies (i.e., antibodies binding to soft tissue antigens other than the α-gal epitopes) in serum samples from the transplanted monkeys. At least two ml blood samples are drawn from the transplanted monkeys on the day of implant surgery and at periodic (e.g., two week) intervals post-transplantation. The blood samples are centrifuged and the serum samples are frozen and evaluated for the anti-Gal and other non-anti-Gal anti-collagen-containing material antibody activity.

Anti-Gal activity is determined in the serum samples in ELISA with α-gal-BSA as solid phase antigen, according to methods known in the prior art, such as, for example, the methods described in Galili et al., *Transplantation* 63: 645-651 (1997).

Assays are conducted to determine whether α-galactosidase treated collagen-containing material induce the formation of anti-collagen antibodies. For measuring anti-soft tissue antibody activity, ELISA assays are performed according to methods known in the prior art, such as, for example, the methods described in K. R. Stone et al., *Transplantation* 63: 640-645 (1997).

The collagen-containing material specimens are optionally explanted at one to two months post-transplantation, sectioned and stained for histological evaluation of inflammatory infiltrates. Post-transplantation changes in anti-Gal and other anti-cartilage soft tissue antibody activities are correlated with the inflammatory histologic characteristics (i.e., granulocytes or mononuclear cell infiltrates) within the explanted soft tissue, one to two months post-transplantation, using methods known in the art, as, for example, the methods described in K. R. Stone et al., *Transplantation* 63: 640-645 (1997).

Injection of Collagen-Containing Material of the Invention

The collagen-containing material of the invention is injectable through a suitable applicator, such as a catheter, a cannula, a needle, a syringe, or a tubular apparatus. The matrix of collagen as a shapeable biomaterial of the present invention may comprise collagen in a form of liquid, colloid, semi-solid, suspended particulate, gel, paste, combination thereof, and the like.

Guidance for the injection of collagen-containing material of the invention into humans is provided by methods for the injection of collagen into humans for soft tissue augmentation. In these methods, the substantially non-immunogenic is introduced to the tissue via conventional needle tip catheter or needle technology using, for example, techniques similar to those used to introduce collagen based soft tissue augmentation materials. Specifically, the injection may be performed through a puncture needle or spinal needle placed directly in the dermis or other tissue to be augmented. Alternatively, in certain situations, the tissue can be exposed surgically and the composition injected directly into the tissue.

The particular amount of polymer composition employed is dictated by various factors such as the size of the correction to be made, the volume to be injected, etc. Such factors are well within the skill of the artisan.

When delivery of the polymeric composition to the tissue is conducted with a small diameter medical catheter (e.g., via a cytoscope), the catheter employed is not critical provided that polymeric catheter components are compatible with the polymeric composition (i.e., the catheter components will not readily degrade or leach in the polymer composition and none of the components of the polymer compositions will readily degrade in the presence of the catheter components). See, e.g., U.S. Pat. Applications 2002/0038152 and 2002/0082594, both incorporated herein by reference. See also, U.S. Pat. Nos. 6,231,613, 6,444,222 and 6,284,284, each incorporated herein by reference.

U.S. Pat. No. 4,803,075, incorporated herein by reference, describes bovine collagen compositions including a lubricant material to enhance injectability through narrow diameter needles for soft tissue repair. U.S. Pat. No. 4,424,208, incorporated herein by reference, describes an injectable dispersion of cross-linked atelopeptide bovine collagen and reconstituted atelopeptide bovine collagen fibers in an aqueous carrier. The atelopeptide form of collagen lacks the native telopeptide cross-linking.

U.S. Pat. Application 2002/0007221 (Jan. 17, 2002), incorporated herein by reference, discloses methods for soft tissue augmentation in a mammal wherein a composition comprising a biocompatible polymer having a water equilibrium content of less than about 15% and a biocompatible solvent is delivered to the tissue of the mammal to be augmented. The biocompatible polymer is selected to be soluble in the biocompatible solvent, but insoluble in the tissue. The biocompatible solvent is miscible or soluble in the fluids of this tissue and, upon contact with such fluids, the biocompatible solvent quickly diffuses away whereupon the biocompatible polymer precipitates to augment the tissue at the delivery site in the mammal.

PCT WO 00/47130, incorporated herein by reference, discloses an injectable collagen-based system defining a matrix of collagen.

PCT WO 01152930, incorporated herein by reference, discloses a method and system for shrinking dilatations of a body, removing excess, weak or diseased tissues and strengthening remaining tissue of the lumen walls, the entire contents of which are incorporated herein by reference.

The details of one or more embodiments of the invention are set forth in the accompanying description above. Although any methods and materials similar or equivalent to those described herein can be used in the practice or testing of the invention, the preferred methods and materials are now described. Those of skill in the art will recognize that the invention may be embodied in other specific forms without departing from the spirit or essential characteristics thereof.

Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The foregoing description has been presented only for the purposes of illustration and is not intended to limit the invention to the precise form disclosed, but by the claims appended hereto.

What is claimed is:

1. A xenogeneic, substantially non-immunogenic collagen-containing material for injection into a human, the collagen-containing material having extracellular components and dead chondrocyte cells with retained native surface glycoproteins substantially lacking immunogenic terminal alpha-1,3-Galactose oligosaccharide structures.

2. The collagen-containing material according to claim 1 in a form of liquid, colloid, semi-solid suspended particulate, gel or paste and combinations thereof.

3. The collagen-containing material of according to claim 2 wherein the collagen-containing material includes extracellular components and substantially only dead cells, the extracellular components and dead cells having substantially no surface alpha-galactosyl moieties and having capping molecules linked to at least a portion of surface carbohydrate moieties.

4. The collagen-containing material according to claim 2 wherein said collagen-containing material is sterilized pursuant to e-beam ionization irradiation.

5. The collagen-containing material according to claim 4, wherein said sterilization is with a radiation dose approximately equal to 17.8 kGy.

6. The collagen-containing material according to claim 1 irradiated with gamma radiation in the amount of 0.2 MegaRad to about 3 MegaRad.

* * * * *